(12) United States Patent
Bruinsma

(10) Patent No.: US 7,392,091 B2
(45) Date of Patent: Jun. 24, 2008

(54) IMPLANTED ANTENNA AND RADIO COMMUNICATIONS LINK

(75) Inventor: Ian Bruinsma, Kings Langley (AU)

(73) Assignee: Cochlear Limited, Lane Cove, NSW (AU)

( * ) Notice: Subject to any disclaimer, the term of this patent is extended or adjusted under 35 U.S.C. 154(b) by 267 days.

(21) Appl. No.: 11/024,707

(22) Filed: Dec. 30, 2004

(65) Prior Publication Data

US 2005/0154428 A1   Jul. 14, 2005

(30) Foreign Application Priority Data

Dec. 30, 2003 (AU) ............................. 2003907152
Dec. 30, 2003 (AU) ............................. 2003907153

(51) Int. Cl.
*A61N 1/08* (2006.01)

(52) U.S. Cl. ........................................ 607/60
(58) Field of Classification Search .................. 607/60, 607/30, 32

See application file for complete search history.

(56) References Cited

U.S. PATENT DOCUMENTS 6,115,636 A * 9/2000 Ryan ............................ 607/60
6,574,510 B2 * 6/2003 Von Arx et al. ............... 607/60

* cited by examiner

*Primary Examiner*—Carl H. Layno
*Assistant Examiner*—Eric D Bertram
(74) *Attorney, Agent, or Firm*—Connolly Bove Lodge & Hutz LLP

(57) ABSTRACT

A medical implant comprising a housing and an antenna member carried by the housing. The antenna member is configured to be capacitively coupled to body tissue in which the housing is implanted. This forms, together with the impedance of the body tissue, part of a resonant circuit. A reference electrode carried by the housing as a return for the antenna member also forms a further part of the resonant circuit. Transceiver circuitry is also provided and is operable as at least one of a source and a load for the antenna member and forms yet a further part of the series resonant circuit.

11 Claims, 3 Drawing Sheets

IMPLANTED ANTENNA AND RADIO COMMUNICATIONS LINK

CROSS-REFERENCE TO RELATED APPLICATIONS

The present application claims priority from Provisional Patent Application Nos 2003907152 and 2003907153 filed on 30 Dec. 2003, the contents of which are incorporated herein by reference.

BACKGROUND

Implantable devices in body tissue which operate at the Medical Implant Communications Service (MICS) frequency need to overcome the lossy medium created by body tissue.

Antennas operate most efficiently at a dimension which is a quarter of a wavelength of signals transmitted or received by the antenna. However, using the MICS frequency range the optimum quarter wavelength would result in an antenna having dimensions of approximately 0.2 m. An antenna of this length would be exceedingly difficult to implant into a patient without significant surgical invasion and discomfort to the patient.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

According to a first aspect of the invention, there is provided a medical implant comprising:
 a housing;
 an antenna member carried by the housing, the antenna member being configured to be capacitively coupled to body tissue in which the housing is implanted to form, together with the impedance of the body tissue, part of a resonant circuit;
 a reference electrode carried by the housing as a return for the antenna member, the reference electrode forming a further part of the resonant circuit; and
 transceiver circuitry operable as at least one of a source and a load for the antenna member and forming yet a further part of the series resonant circuit.

According to a second aspect of the invention, there is provided a method of transmitting a signal between a medical implant and an external unit arranged externally of a patient's body, the method including the steps of:
 feeding signals to an antenna member of the implant, the antenna member being capacitively coupled to body tissue in which the implant is arranged; and
 using the capacitively coupled body tissue as an extension of the antenna to transmit the signals between the implant and the external unit.

In one embodiment, the resonant circuit can be a series resonant circuit. The series resonant circuit may be completed by an impedance matching network which is arranged between the antenna member and the transceiver circuitry. The impedance matching network may comprise an inductor and other components. The impedance matching network may be used to transform a total load impedance of the body tissue and the antenna member capacitance to a value optimised for maximum power transfer between the transceiver circuitry and the body tissue.

The impedance matching network may further perform other optimisation and signal coupling/decoupling functions.

The impedance matching network may be electrically adjustable to compensate for varied implant conditions.

In another form of the invention, the antenna member may be arranged within the housing. The housing may therefore be a radio opaque housing to allow strong capacitive coupling through to the body tissue. The housing may be sufficiently thin to create a capacitance between the antenna member and the body tissue and may further be arranged to have a high dielectric co-efficient to increase the capacitance.

In yet another form of the invention, the antenna member may be arranged externally on the housing to be in direct contact with the body tissue when the housing is implanted. In this case, the impedance matching network may contain a low frequency block to isolate low frequency stimulation currents.

The reference electrode may be arranged externally of the housing to be in direct contact with the tissue. Instead, the reference electrode may be capacitively isolated from the body tissue by being placed within the housing. It will be appreciated that the reference electrode and the antenna member are capacitively coupled to each other.

The transceiver circuitry may comprise a radio frequency circuit which allows communication in the MICS frequency band. The transceiver circuitry may contain a combination of a transmitter, a receiver, a demodulator, a detector and related signal processing circuitry.

Where the implant is used as a stimulation device, for example, a functional electrical stimulation (FES) device, the housing may contain a stimulation drive circuit module. The stimulation drive circuit module may communicate with the transceiver circuitry via a data link. The data link may be a digital radio data and control link. The stimulation drive circuit module may generate the required signals for stimulation, may monitor the condition of an internal battery of the implant and may be microprocessor controlled.

The antenna member may be arranged to capacitively couple RF current into the body tissue. Thus, the antenna member may have a surface area large enough to effect capacitive coupling between the antenna member and the body tissue. However, because the capacitance of the body tissue at the MICS frequencies is significantly smaller than that of the antenna/body tissue capacitance, the dominant capacitance is the body tissue capacitance.

According to a third aspect of the invention, there is provided a medical implant which includes:
 a housing;
 control circuitry contained within the housing;
 a plurality of electrodes each of which is connected via a lead to the control circuitry; and
 a frequency-dependent isolating module interposed between at least one of the electrode leads and the control circuitry to permit the at least one electrode and its lead to function as an antenna for transmission of signals between the control circuitry and an external unit arranged externally of a patient's body.

According to a fourth aspect of the invention, there is provided a method of transmitting signals between an implanted medical implant and an external unit arranged externally of a patient's body, the implant including a plurality of electrodes each of which is connected by an electrode lead to control circuitry in a housing of the implant, the method including the steps of:

generating signals to be transmitted to or from the implant;

electrically coupling at least one of the electrodes and its associated lead to the control circuitry of the implant; and using the at leat one electrode and its associated lead as an antenna to effect transmission of signals between the implant and the external unit.

As indicated above in the third and fourth aspects, the implant may include a plurality of electrodes each of which is connected to the control circuitry via a lead. Each lead may feed through the housing of the implant through a hermetically sealed feed through element.

The control circuitry of the third and fourth aspects may include transceiver circuitry which feeds data, at a radio frequency, to, and which receives radio signals from, the external unit. The transceiver circuitry may also include an impedance matching network for the electrode and lead functioning as the antenna.

The control circuitry may further include a stimulation circuit module which contains the electronics for the predetermined stimulation application of the implant. The stimulation circuit module may be microprocessor controlled and may include a battery for operation of the implant, associated electronics, measurement circuitry and, optionally, other radio transceivers.

The frequency-dependent isolating module of the third aspect by which the electrode and its associated lead are connected to the control circuitry may comprise, firstly, a radio frequency choke which passes a lower frequency stimulation signal to enable the electrode to operate as a stimulation electrode, the radio frequency choke further blocking higher, radio frequency signals. Further, the isolating module may include a radio frequency coupling element which blocks the low frequency stimulation signal and couples the radio frequency signal to ground.

Optionally, certain additional electrodes with their associated leads may be used as ground references for the antenna in addition to being used as electrodes for stimulation purposes. These additional electrodes may be coupled to the control circuitry via isolating modules as well. Hence, each of the additional electrodes may be connected to the control circuitry via a radio frequency choke which passes a low frequency stimulation signal but which blocks the radio frequency signal and a ground radio frequency coupling which blocks the low frequency stimulation signal and couples the radio frequency signal to ground.

Each of the remaining electrodes with their associated electrode leads may be coupled to the control circuitry via radio frequency chokes which, once again, pass the lower frequency stimulation signals but block the radio frequency signals.

The implant of the third and fourth aspects may further include a return electrode plate mounted on the housing. The electrode plate may be mounted externally on the housing to be in direct contact with body tissue in which the implant is implanted. Instead, the electrode plate may be mounted within the housing to be isolated from direct contact with the body tissue but which still allows capacitive coupling to the body tissue.

The electrode used as the antenna may be radio frequency isolated from the body tissue by manufacturing a choke-inline with the antenna electrode at the appropriate length. Instead, the antenna may have the electrode capacitively coupled to the body tissue so that the body tissue is used as an extension of the antenna.

BRIEF DESCRIPTION OF THE DRAWINGS

The invention is now described by way of example with reference to the accompanying drawings in which.

DETAILED DESCRIPTION

Figure 1:
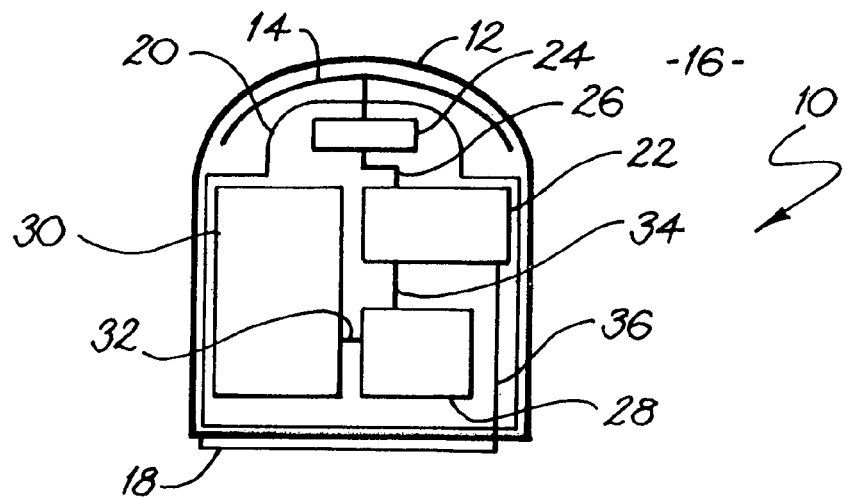
FIG. 1 shows a schematic representation of a medical implant, in accordance with an embodiment of the invention.
Figure 2:
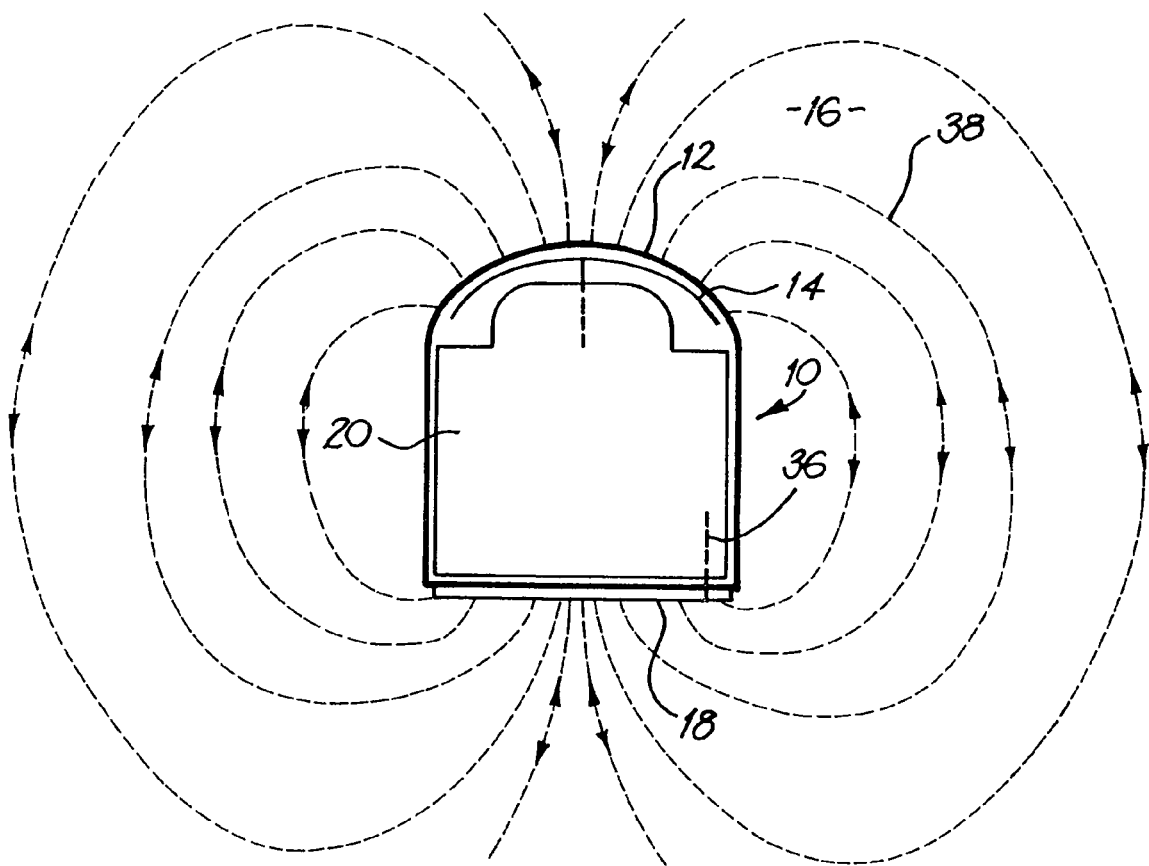
FIG. 2 shows a schematic representation of current generated in body tissue as a result of a capacitive coupling of the implant to the body tissue.
Figure 3:
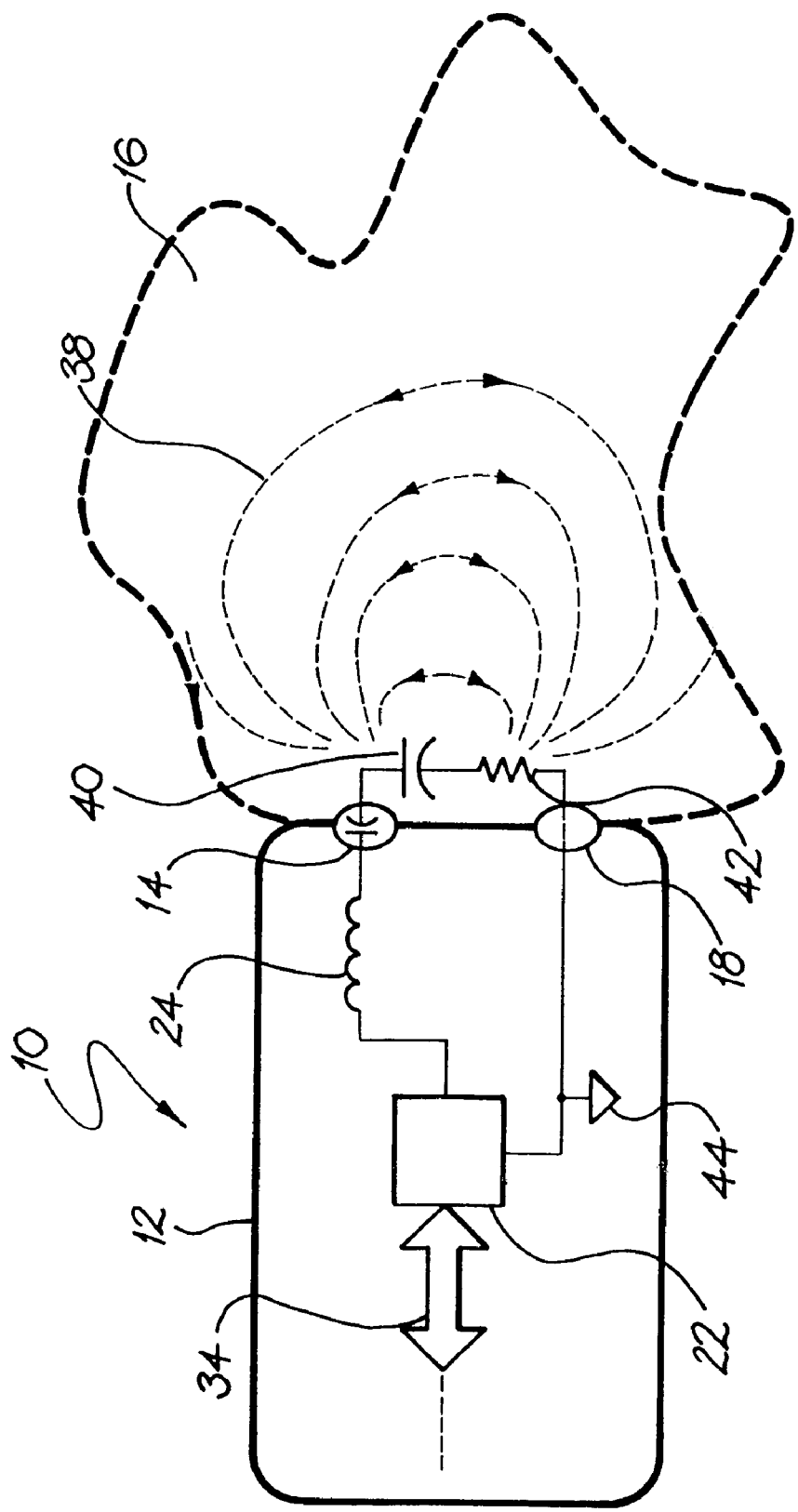
FIG. 3 shows a simplified equivalent circuit of the representation of FIG. 2.

As shown in FIGS. 1-3, reference numeral 10 generally designates a medical implant, in accordance with one embodiment of the invention. The implant 10 includes a ceramic or radio opaque housing 12 to allow strong capacitive (high value) coupling between an antenna member 14 arranged within the housing 12 and body tissue, indicated generally at 16, in which the implant 10 is implanted.

The implant 10 includes a return electrode 18 which, in this embodiment of the invention, is arranged externally of the housing 12. The electrode 18, which is in the form of an electrode plate, provides a connection to the body tissue 16 of the patient and acts as a return current path for radio signals from the antenna member 14. The electrode 18, can also be used as a return electrode for a stimulation signal generated by the implant 10.

Optionally, the return electrode 18 can be mounted within the housing 12 to be capacitively coupled to the body tissue 16.

The antenna member 14 is in the form of a plate and is designed to capacitively couple RF current into the body tissue 16. As illustrated, the antenna plate 14 is mounted under the surface of the housing 12. The plate 14 has a surface area large enough to create a large capacitance between the antenna plate 14 and the body tissue 16. This capacitance is large compared to the tissue capacitance of the body tissue 16 at the MICS frequency used for the implant 10. Thus, the total antenna load is dominated by the body tissue capacitance, allowing the body tissue to perform the major role in the antenna resonant circuit. Typically, the capacitance of the antenna plate 14 to the body tissue 16 is an order of magnitude greater than the capacitance of the body tissue 16.

Because the antenna plate 14 is arranged within the housing 12, it is not in physical contact with the body tissue. This has the advantage that the antenna plate 14 can be made of any suitable conducting metal to optimise the radio frequency characteristics and need not be made of bio-compatible metal. In addition, the antenna plate 14 could be a part of a printed circuit board 20 on which components of the implant 10 are arranged. It will be appreciated that, in an embodiment (not shown) where the antenna plate 14 is arranged externally of the housing 12, the antenna plate 14 needs to be of a suitable bio-compatible implantable metal such as platinum, titanium, stainless steel, or the like.

The implant 10 includes transceiver circuitry 22. This circuitry 22 is a radio frequency circuit that allows communication on the MICS frequency band. The circuitry 22 contains a combination of transmitter, receiver, demodulator, detector and signal processing. The antenna plate 14 is connected to the circuitry 22 via an impedance matching network 24. Typically, the impedance matching network 24 is a passive inductor and capacitor network.

The impedance matching network 24 is used to transform the total load impedance comprising the capacitance between the antenna plate 14 and the body tissue 16 to a value optimised for maximum power transfer between the transceiver circuit 22 and the body tissue 16, enabling the body tissue to radiate the radio frequency signal.

The impedance matching network 24 also performs secondary functions and may contain other circuit items to optimise voltages, optimise the current, optimise the impedance, protect the transceiver circuit 22, effect power saving, effect other signal coupling or decoupling and filter unwanted signals. The impedance matching network 24 is designed to have low radio frequency losses.

In the case where the antenna plate 14 is mounted externally of the housing 12 in direct contact with the body tissue 16, the impedance matching network contains a low frequency block to isolate the low frequency stimulation tissue currents when the implant 10 is operable as a stimulation device. In this regard it is also to be noted that, where the implant 10 operates as a stimulation device, the return electrode 18 could operate as a return path for stimulation currents.

The impedance matching network 24 is connected to the transceiver circuit 22 via a link 26. The link 26 couples RF power in both directions between the transceiver circuit 22 and the impedance matching network 24.

As indicated above, the implant 10 could operate as a stimulation device such as, for example, a functional electrical stimulation (FES) device. Thus, the implant 10 includes a stimulation drive circuit module 28. The module 28 is microprocessor controlled and generates the required signals for stimulation. The implant 10 is battery operated via an internal battery 30. The module 28 monitors the condition of the battery 30 via a connection 32.

The module 28 communicates with the transceiver circuitry 22 via a link 34. The link 34 is a digital radio data and control link for effecting exchange of digital data and control signals between the module 28 and the transceiver circuitry 22.

Finally, a connection 36 is provided for establishing electrical connection between the transceiver circuitry 22 and the return electrode 18. This connection 36 couples RF power in both directions between the transceiver circuitry 22 and the return electrode 18. In use, data to be fed from the implant 10 to an external control unit (not shown) arranged externally of the patient's body is transmitted from the transceiver circuitry 22 to the antenna plate 14. The antenna plate 14 is configured to be capacitively coupled with the body tissue 16 such that radio frequency currents, as represented schematically at 38 in FIG. 2 of the drawings, are generated in the body tissue 16. This current is distributed in the body tissue 16 and causes a radiation effect similar to an antenna point source in a lossy medium. In other words, the body tissue 16 functions as part of the antenna of the implant 10 and effects energy transfer to the external unit. Hence, the need for a physically large antenna 14 for the implant 10 is obviated.

In this regard it is to be noted that the implant 10 functions in the MICS frequency band which is in the range 402 MHz to 405 MHz. A quarter wavelength antenna for such a frequency band would have a physical dimension of approximately 20 cm. With the use of the body tissue 16 as part of the antenna structure, the antenna plate 14 need not have such a large dimension.

Because the housing 12 is radio opaque, other electromagnetic signals can be transmitted to the implant 10, for example, an inductive coil for recharging the battery 30 or to add additional current when high stimulation currents are required.

Referring to FIG. 3, it is to be noted that the antenna plate 14 together with the impedance of the body tissue 16 forms part of a series resonant circuit to effect energy transfer into the body tissue 16.

The antenna plate 14 is represented in the series resonant circuit as a capacitor due to its mounting in the housing 12 and being capacitively coupled to the body tissue 16. Because the antenna plate 14 is mounted within the housing 12 it need not be of a biocompatible material and is a copper plate.

The body tissue 16 is represented as a capacitance 40 of the series resonant circuit and a resistor 42. The resistor 42 represents the resistive losses in the body tissue 16 and is a first order representation of all body tissue losses lumped together and lowers the Q of the circuit.

The series resonant circuit has a ground 44 to which the return electrode 18 is connected.

Finally, the series resonant circuit is completed by the transceiver circuitry 22 and the impedance matching network 24. The impedance matching network 24 is represented as an inductance in the series resonant circuit.

It is therefore an advantage of this embodiment of the invention that an implant 10 and method are provided which uses the body tissue 16 as an extension of the antenna 14 of the implant resulting in higher radiated radio energy, reduced power requirements, longer life of the battery 30, an increased operating range and no dependence on the antenna 14 being close to a surface of the skin of the patient. In addition, because of the capacitive coupling between the antenna plate 14 and the body tissue 16, the orientation of the implant 10 is less critical resulting in a greater choice of implant locations. In addition, the implant 10 can be mounted deeper within the body tissue 16 without significant signal loss.

Also, the size of the antenna plate 14 can be reduced resulting in a smaller implant 10 overall.

The capacitive coupling of the antenna plate 14 to the body tissue results in higher efficiency than a metal patch on top of a titanium shell or housing as the ground return is close to the antenna. There is more radiated radio energy through the body tissue resulting in reduced power requirements, increased operating range, etc.

A further major advantage of this embodiment of the invention is that, because the antenna plate 14 is preferably arranged within the housing 12, the antenna plate 14 need not be of a biocompatible material. Thus, a lower cost metal can be use which is also more efficient for signal transmission than biocompatible metals.

In addition, no feedthrough to the antenna plate 14 is required allowing for easier manufacturing of the housing 12 without the need for additional sealing arrangements thereby increasing the reliability of the implant 10. As indicated above, the antenna plate 14 can be part of the printed circuit board 20, thereby further facilitating manufacture of the implant 10 and obviating the need for mechanical connection between the antenna plate 14 and the other circuitry.

A further advantage of this embodiment of the invention is that testing on the antenna plate 14 and the transceiver circuitry 22 can be carried out before they are placed in the housing 12 which is also beneficial from a manufacturing point of view.

Importantly, the characteristic impedance of the series resonant circuit is relatively constant because the antenna plate 14 is not in contact with the tissue thereby providing for improved power transfer.

In this regard, a simple impedance matching network 24 may be used being, typically, a series inductor. This allows fewer components in the implant 10 thereby reducing its size and resulting in lower losses in the impedance matching circuit 24. In contrast, where a patch-type antenna is arranged on the outside of a titanium shell, the capacitance is very high requiring larger lossy inductors and capacitors in the impedance matching network.

The antenna resonance is set up in the body tissue 16 as part of the antenna load and is therefore first generated and then coupled to the body tissue. This results in increased radio efficiency.

The same antenna plate 14 can be optimised for use at multiple frequencies when communicating on different radio bands. The antenna plate size and shape is not important to optimise radiated power. The only change required is to the impedance matching network 24. This results in a reduced size and weight of the implant 10 and reduces the number of antennas 14 required for various applications. It also keeps the antenna design efficient for designs involving multiple communication frequencies and bands.

Figure 4:
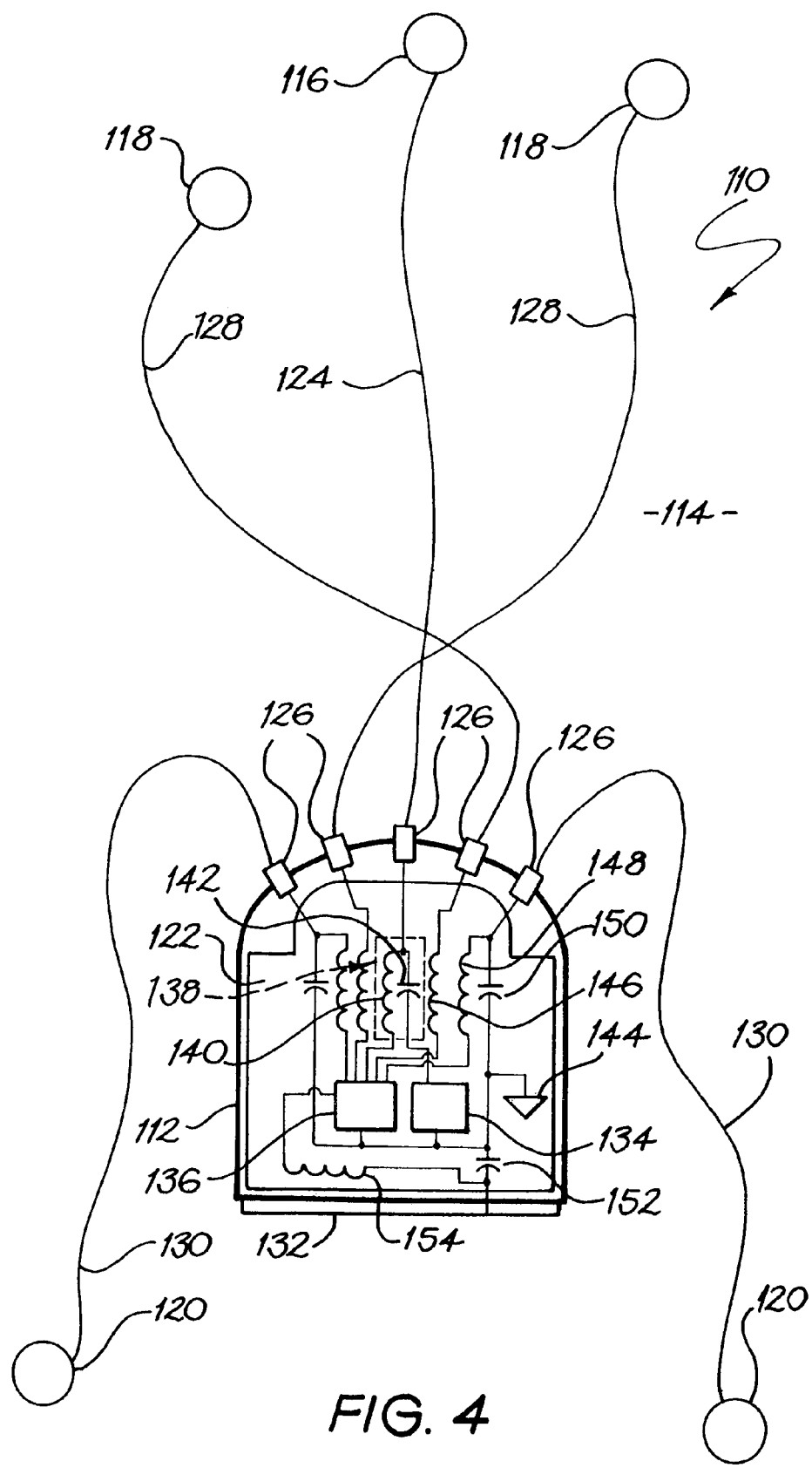
FIG. 4 shows a schematic representation of a medical implant, in accordance with an alternative embodiment of the invention.

Another embodiment of the present invention is shown in FIG. 4. As in the previously described embodiment, the implant 110 includes a housing 112 to be implanted in tissue, represented generally at 114, of a patient's body. The implant 110 includes a plurality of electrodes 116, 118 and 120. It will be appreciated that, depending on the application of the implant 110, a larger number or a fewer number of electrodes 116, 18 and 120 could be provided.

The implant 110 includes control circuitry 122 arranged within the housing 112.

The electrode 116 is connected via an electrode lead 124 and through one of a plurality of feedthroughs 126 to the control circuitry 122. Each electrode 18 is connected via an electrode lead 128 to the control circuitry 122. Similarly, each electrode 120 is connected via an electrode lead 130 to the control circuitry 122. As is the case with the electrode lead 124, each of the electrode leads 128 and 130 is connected to the control circuitry 122 via one of the feed throughs 126.

The implant 110 includes a reference electrode plate 132 arranged on an outside of the housing 112.

The control circuitry 122 includes transceiver circuitry 134. The transceiver circuitry 134 generates radio frequency signals to be transmitted to an external unit (not show) which communicates with the implant 110. It also receives radio frequency signals from the external unit. In addition, the transceiver circuitry 134 includes an impedance matching network for matching the electrode 116 and its lead 124 when operating as an antenna, as will be described in greater detail below.

The control circuitry 122 further includes a stimulation circuit module 136. The module 136 contains electronics for effecting stimulation of the patient's body via the electrodes 116, 118 and 120. The module 136 may be microprocessor controlled and also monitors the condition of a battery (not shown) by means of which the implant 110 is powered. Optionally, the module 136 includes measurement circuitry, other radio transceivers and related circuitry.

The electrode 116 and its associated lead 124 can operate either as a stimulation electrode for effecting stimulation at the site of the patient's body at which the electrode 116 is located. Additionally, the electrode 116 with its associated lead 124 can also function as an antenna for effecting communication between the transceiver unit 134 of the implant 110 and the external unit. The electrode 116 and its lead 124 are therefore connected to the control circuitry via a frequency-dependent isolating module 138. The isolating module 138 comprises a radio frequency choke 140 via which the electrode lead 124 is connected to the stimulation circuit module 136 of the control circuitry 122. The choke 140 passes the low frequency stimulation signal when the electrode 116 is operating as a stimulation electrode. The choke 140 blocks the higher, radio frequency signal.

The module 138 further includes a radio frequency coupling element 142 via which the electrode lead 124 is connected to the transceiver circuitry 134. The element 142 shows a high impedance to, and therefore blocks, the low frequency stimulation signal to the electrode 116 but couples, by presenting a low impedance, the radio frequency signal to ground 144.

In this example, it is assumed that the electrodes 118 serve only as stimulation electrodes. Each lead 128 of the electrodes 118 is therefore connected to the stimulation circuit module 136 of the control circuitry 122 via a radio frequency choke 146 which functions in the same manner as the choke 140.

When the electrode 116 and its lead 124 are being used as an antenna, additional electrodes 120 are used as an RF ground reference. The lead 130 from each electrode 120 is therefore connected to the stimulation circuit 136 of the control circuitry 122 via a radio frequency choke 148. Each of these chokes 148 functions in the same manner as the chokes 140 and 146. A ground, radio frequency short 150 connects each lead 130 to ground 144 at radio frequency. The short 150 presents a high impedance to the low frequency stimulation signal and therefore blocks the low frequency stimulation signal while presenting a low impedance for the radio frequency signal to couple the radio frequency signal to ground.

An optional ground radio frequency short 152 and an optional radio frequency choke 154 are also provided which perform the same functions as the other shorts and chokes as described above.

In use, when it is desired to transmit data from the implant to the external unit, the electrode 116 with its lead 124 functions as an antenna with the electrodes 120 and their leads 130 functioning as a ground reference for the antenna. The radio frequency signal is passed by the element 142 while any stimulation signal from the stimulation circuit module 136 is blocked by the choke 140. Similarly, when a radio frequency signal is received by the implant 110, the electrode 116, with its lead 124, functions as an antenna with the radio frequency signal being passed by the element 142 to the transceiver circuit 134.

If desired, the electrode 116 could be capacitively coupled to the body tissue 114 of the patient so that the body tissue 114 functions as an extension of the antenna in the manner as described above. Instead, the electrode 116 could be isolated from the body tissue 114 by placing an inductor choke (not shown) along the length of the lead 124 at the appropriate location. The choke may be manufactured into the lead 124 by creating a coil in the wire as shown by reference numeral 151.

It is also to be noted that, instead of having the electrode plate 132 arranged externally of the housing 112, it could be arranged within the housing being coupled capacitively through the wall of the housing 112 to the body tissue 114.

It is also to be noted that, if one of the electrodes is to be used as a dedicated antenna, the need for the choke 140 is obviated.

While the implant 110 is intended to operate in the MICS frequency band, the implant 110 could be optimised for use at multiple frequencies communicating on different radio bands. The only change that is required is to the matching network of the transceiver circuitry 134.

The lead 124 can be made longer than the electrode requirements alone. This allows the lead to be placed close to the surface of the patient's skin with the implant 110 in a more optimum location and to provide better transmission signal levels.

It is an advantage of this embodiment of the invention that an existing electrode of the implant 110, with its associated lead, is used as the implant antenna. Optimisation of the length of the lead can result in greater radiated radio energy, reduced power requirements, longer battery life, increased operating range and no dependence on the antenna being located near the surface of the patient's skin. In addition, orientation of the implant is less critical resulting in a greater choice of implant locations. Still further, the implant 110 can be mounted deeper in the body tissue without significant signal loss.

Because the antenna is realised by way of the electrode 116 and its lead 124, the implant 110 does not have to be sufficiently large to incorporate a typical antenna. Thus, the physical size of the housing 112 of the implant 110 can be reduced which simplifies implantation and results in reduced patient discomfort.

Because one of the existing electrode leads 124 is being used as the antenna, no additional feedthroughs are required in the housing 112 thereby reducing the cost of providing for hermetic sealing of the housing 112 and reducing the cost of manufacture in general.

If the feedthroughs 126 are in the form of connectors, the desired length of antenna can be selected at surgery when the electrodes are placed. This allows tailoring of the antenna for the application of the implant 110 and further facilitates manufacture and reduces manufacturing costs.

Common techniques for creating small antennas require the use of large amounts of dielectric material which is usually heavy. This requirement is obviated by the present which results in a reduction in the weight of the housing 112 of the implant 110 and provides a greater choice of implant locations.

The same antenna design can be optimised for use with multiple frequencies to facilitate communication over different radio frequency bands. This results in further reduction in size of the implant, reduces the need for a number of antennas, reduces the weight of the implant 110, is less invasive for the patient and keeps the antenna design efficient for designs involving multiple communications frequency bands.

In each of the above described embodiments of the invention, the transmission of signals between the implanted device and an external unit is facilitated by adapting a part of the device and/or the surrounding tissue to function as part of the antenna means. Such an adaptive system enables the size and construction of implantable medical devices to be readily optimised, thereby providing more access to medical devices for treatment of a variety of medical conditions.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A medical implant comprising:
   a housing;
   a reference electrode plate mounted on the housing and configured to be in direct contact with a body tissue, control circuitry contained within the housing;
   a plurality of electrodes each of which is connected via a lead to the control circuitry; and
   a frequency-dependent isolating module interposed between the lead of a selected electrode of the plurality of electrodes and the control circuitry, the frequency-dependent isolating module for blocking stimulation signals generated by control circuitry to permit the selected electrode and its lead, reference electrode plate, and body tissue to form a resonant circuit to function as an antenna for transmission of signals between the control circuitry and an external unit arranged externally of a patient's body.

2. A medical implant according to claim 1, wherein each lead is fed through the housing of the implant through a hermetically sealed feedthrough element.

3. A medical implant according to claim 1, wherein the control circuitry includes transceiver circuitry which feeds data, at a radio frequency, to the external unit.

4. A medical implant according to claim 3, wherein the transceiver circuitry includes an impedance matching network for the electrode and lead functioning as the antenna.

5. A medical implant according to claim 1, wherein the control circuitry includes transceiver circuitry which receives radio signals from the external unit.

6. A medical implant according to claim 1, wherein the control circuitry further includes a stimulation circuit module which contains the electronics for generating the stimulation signals for application to the patient's body via the electrodes.

7. A medical implant according to claim 6, wherein the stimulation circuit module is microprocessor controlled and includes a battery for operation of the implant.

8. A medical implant according to claim 1, wherein the frequency-dependant isolating module comprises, a radio frequency choke which passes the stimulation signals and blocks higher frequency radio signals to enable the selected electrode to operate as a stimulation electrode.

9. A medical implant according to claim 1, wherein additional electrodes of the plurality of electrodes and their associated leads are used as ground references for the antenna and for stimulation purposes.

10. A medical implant according to claim 9, wherein the additional electrodes are coupled to the control circuitry via isolating modules.

11. A medical implant according to claim 1, wherein the selected electrode is radio frequency isolated from the body tissue by providing a choke in-line with the selected electrode at an appropriate length.

* * * * *

UNITED STATES PATENT AND TRADEMARK OFFICE
CERTIFICATE OF CORRECTION

| | |
|---|---|
| PATENT NO. | : 7,392,091 B2 |
| APPLICATION NO. | : 11/024707 |
| DATED | : June 24, 2008 |
| INVENTOR(S) | : Bruinsma |

It is certified that error appears in the above-identified patent and that said Letters Patent is hereby corrected as shown below:

In the Specification:

Page 5, column 1, line 13 the Field of the Invention paragraph was omitted in its entirety, it should read as follows:

-- Field of the Invention
This invention relates generally to the field of implantable medical devices and, more specifically, to the field of implantable devices which communicate with external units. More particularly, the invention relates to a medical implant and to a method of transmitting signals between an implanted medical implant and an external unit. --

Column 3, line 1 reads "using the at leat one electrode and its associated lead as an", it should read -- using at least one electrode and its associated lead as an --.

Column 6, line 54 reads "be use which is also more efficient for signal transmission", it should read -- be used which is also more efficient for signal transmission --.

Column 7, line 36 reads "116, 18 and 120 could be provided.", it should read -- 116, 118 and 120 could be provided. --.

Column 7, line 41 reads "control circuitry 122. Each electrode 18 is connected via an", it should read -- control circuitry 122. Each electrode 118 is connected via an --.

Column 7, line 51 reads "signals to be transmitted to an external unit (not show) which", it should read -- signals to be transmitted to an external unit (not shown) which --.

UNITED STATES PATENT AND TRADEMARK OFFICE
CERTIFICATE OF CORRECTION

| | |
|---|---|
| PATENT NO. | : 7,392,091 B2 |
| APPLICATION NO. | : 11/024707 |
| DATED | : June 24, 2008 |
| INVENTOR(S) | : Bruinsma |

It is certified that error appears in the above-identified patent and that said Letters Patent is hereby corrected as shown below:

Column 9, line 25 reads "Because the antenna is realised by way of the electrode", it should read -- Because the antenna is realized by way of the electrode --.

Column 10, beginning with line 31: The claim reads "A medical implant according to claim 3, wherein the transceiver circuitry includes an impedance matching net-work for the electrode and lead functioning as the antenna.", it should read -- A medical implant according to claim 1, wherein the control circuitry includes transceiver circuitry which receives radio signals from the external unit. --

Column 10, beginning with line 34: The claim reads "A medical implant according to claim 1, wherein the control circuitry includes transceiver circuitry which receives radio signals from the external unit.", it should read -- A medical implant according to claim 3, wherein the transceiver circuitry includes an impedance matching network for the electrode and lead functioning as the antenna. --

Column 10, line 45: reads "frequency-dependant isolating module comprises, a radio", it should read -- frequency-dependent isolating module comprises, a radio --.

Signed and Sealed this

Thirtieth Day of September, 2008

JON W. DUDAS
*Director of the United States Patent and Trademark Office*